United States Patent
Markham et al.

(10) Patent No.: US 9,014,816 B2
(45) Date of Patent: Apr. 21, 2015

(54) MEDICAL LEAD WITH FILLER LAYER

(75) Inventors: Jacob E. Markham, Vadnais Heights, MN (US); John W. Warling, Maplewood, MN (US); Victoria K. Sandberg, Stacy, MN (US)

(73) Assignee: W. C. Heraeus GmbH, Hanau (DE)

( * ) Notice: Subject to any disclaimer, the term of this patent is extended or adjusted under 35 U.S.C. 154(b) by 626 days.

(21) Appl. No.: 12/900,344

(22) Filed: Oct. 7, 2010

(65) Prior Publication Data

US 2012/0089213 A1   Apr. 12, 2012

(51) Int. Cl.
  *A61N 1/05*   (2006.01)
  *A61M 25/09*   (2006.01)

(52) U.S. Cl.
  CPC ..... *A61M 25/09* (2013.01); *A61M 2025/09066* (2013.01); *A61M 2025/09108* (2013.01); *A61M 2025/09166* (2013.01); *A61N 1/05* (2013.01)

(58) Field of Classification Search
  USPC .................. 607/115, 116, 119, 122
  See application file for complete search history.

(56) References Cited

U.S. PATENT DOCUMENTS

| | | | |
|---|---|---|---|
| 5,439,485 A * | 8/1995 | Mar et al. | 607/119 |
| 5,807,279 A | 9/1998 | Viera | |
| 6,673,025 B1 | 1/2004 | Richardson et al. | |
| 7,277,762 B2 | 10/2007 | Belden et al. | |
| 7,455,646 B2 | 11/2008 | Richardson et al. | |
| 7,494,474 B2 | 2/2009 | Richardson et al. | |
| 7,553,287 B2 | 6/2009 | Reynolds et al. | |
| 7,612,291 B2 | 11/2009 | Chastain et al. | |
| 7,641,647 B2 | 1/2010 | Gunderson | |
| 2004/0215298 A1 * | 10/2004 | Richardson et al. | 607/115 |
| 2010/0049290 A1 * | 2/2010 | Min et al. | 607/127 |
| 2010/0268310 A1 * | 10/2010 | Bonde et al. | 607/116 |
| 2011/0034979 A1 * | 2/2011 | Min et al. | 607/116 |

* cited by examiner

*Primary Examiner* — Kennedy Schaetzle
*Assistant Examiner* — Erica Lee
(74) *Attorney, Agent, or Firm* — Dicke, Billig & Czaja, PLLC

(57) ABSTRACT

A medical lead includes a first wire coil having an outer diameter and a marker coil having an inner diameter. The marker coil is assembled over the first wire coil. The outer diameter first wire coil is smaller than the inner diameter of the marker coil thereby defining a gap. A second wire coil substantially fills the gap between the first wire coil and the marker coil. A ball weld is formed at an end of the medical lead adjacent each of the first and second wire coils and adjacent the marker coil.

15 Claims, 3 Drawing Sheets

MEDICAL LEAD WITH FILLER LAYER

BACKGROUND

One aspect relates to a medical lead having a filler layer. More particularly, a medical lead having a filler layer includes a marker coil. Medical leads and intravascular guidewires are used in conjunction with intravascular devices such as catheters to facilitate navigation through the vasculature of a patient. Such guidewires are typically very small in diameter and some include marker bands for in-vivo radiographic visualization. A wide variety of radiopaque marker bands have been developed for intracorporal medical devices. Some of the devices that include marker bands are guidewires and catheters. Of the known marker bands and intracorporal medical devices with marker bands, each has certain advantages and disadvantages. There is an ongoing need to provide alternative designs and methods of making and using marker bands and medical devices with marker bands.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
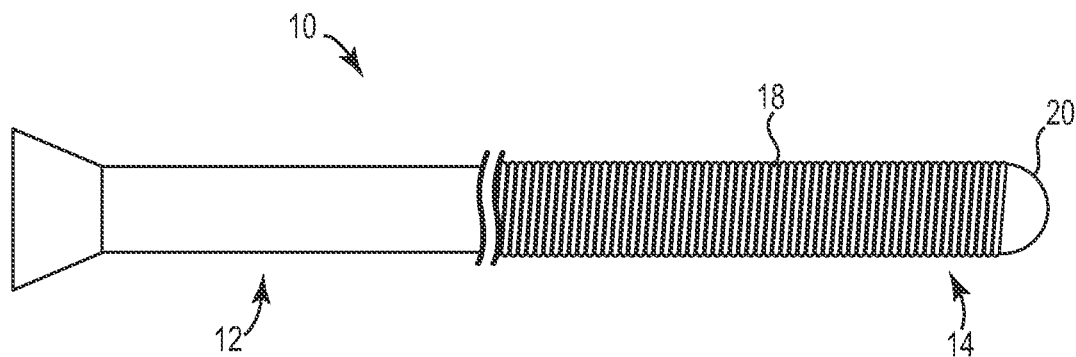
FIG. 1 illustrates a medical lead in accordance with one embodiment.

FIG. 1 illustrates medical lead 10 in accordance with one embodiment. In one embodiment, lead 10 has a proximal section 12 and a distal section 14. In some applications, medical lead 10 is a guide catheter. In such an application, a hub or other mechanism is attached to proximal section 12 for guiding or controlling the medical lead 10. Although medical lead 10 is in one embodiment a guide catheter, medical lead 10 could be any other type of catheter including diagnostic or therapeutic catheters such as angioplasty balloon catheters, atherectomy catheters, stent delivery catheters, and the like, or any other suitable device. Furthermore, medical lead 10 can generally include any device designed to pass through an opening or body lumen. For example, medical lead 10 may comprise an endoscopic device, laproscopic device, embolic protection device, guidewire, and the like, or any other suitable device.

In one embodiment, distal section 14 of medical lead 10 includes marker coil 18, which is assembled over an inner coil (not visible in FIG. 1) adjacent lead tip 20. In one embodiment, marker coil 18 of medical lead 10 is used to aid in the visualization of medical lead 10 in accordance with any number of known visualization techniques, while the medical device is in use within the body. Typically the visualization techniques used rely on marker coil 18 being made from or otherwise including a radiopaque material. Radiopaque materials are materials capable of producing a relatively bright image on a fluoroscopy screen or another imaging technique during a medical procedure. This relatively bright image aids the user of medical lead 10 in determining its location. Some examples of radiopaque materials can include, but are not limited to, gold, platinum, platinum-iridium, palladium, tantalum, tungsten alloy, plastic material loaded with a radiopaque additive, and the like.

In one embodiment, marker coil 18 is assembled about the distal section 14 of medical lead 10 adjacent lead tip 20. Securing the position of marker coil 18 may be important for a number of reasons. For example, if marker coil 18 is properly secured, the clinician can rely on the known position of marker coil 18 in order to accurately assess the position of the remainder of medical lead 10. This may include the clinician being able to know the precise location of the lead tip 20 of medical lead 10 by virtue of visualizing marker coil 18 and knowing that marker coil 18 is adjacent the distal tip 20 of medical lead 10.

Knowing the precise location may be important when medical lead 10 is being used in a particular sensitive location, such as the central nervous system, because errantly positioning the medical lead 10 could damage sensitive areas. It can be appreciated that given the small scale of catheters and blood vessel, even a very small shift in the position of marker coil 18 can have real impact on a medical intervention.

Figure 2A:
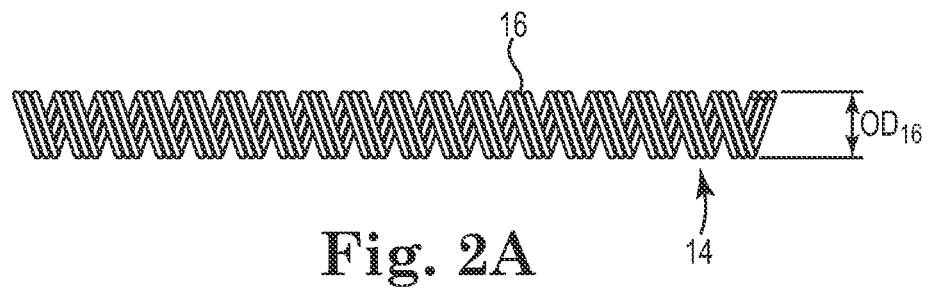
FIG. 2A illustrates a stranded coil of a medical lead in accordance with one embodiment.

FIG. 2A illustrates a portion of distal section 14 of medical lead 10 during assembly. In one embodiment, medical lead 10 is formed starting with its inner coil 16. In one embodiment, inner coil 16 is a stranded coil. In one example, inner coil 16 is a miltifiler coil, that is, a coil with multiple wires stranded together, the combination of which is then helically wound. In one embodiment, the helical winding of inner coil 16 forms an inner lumen, which can be useful in many embodiments. In one example, inner coil 16 can be helically wound over a mandrel that is then subsequently removed. In the illustration, inner coil 16 has an outer diameter $OD_{16}$.

In one embodiment, inner coil 16 is coated with a plastic coating, such as a polytetrafluoroethylene (PTFE) or the like. In one embodiment, the plastic coating on inner coil 16 is removed such that when lead tip 20 is welded to coil 16, the strands of coil 16 are electrically coupled together. In one embodiment, inner coil 16 of medical lead 10 thus functions as a conductor and electrode.

Figure 2B:
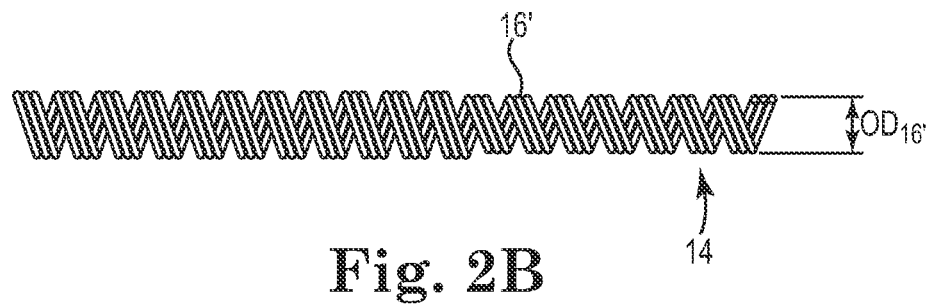
FIG. 2B illustrates a stranded coil of a medical lead in accordance with one embodiment.

In removing the plastic coating from inner coil 16, however, the outer diameter $OD_{16}$ is decreased to a smaller outer diameter $OD_{16'}$, in the region where the coating is removed. FIG. 2B illustrates a portion of distal section 14 of medical lead 10 after the plastic coating is removed from inner coil 16, thereby causing the smaller outer diameter $OD_{16'}$.

When inner coil 16 has a smaller outer diameter $OD_{16'}$, such as can occur after its plastic coating is removed, securing marker coil 18 over it and securing lead tip 20 adjacent to it, can be compromised in some embodiments. Accordingly, in one embodiment, filler layer 17 is assembled over inner coil 16 before securing marker coil 18 over it, and before securing lead tip 20 adjacent to it. In one embodiment, filler layer 17 is assembled over the area where plastic coating is removed from inner coil 16 and has a smaller outer diameter $OD_{16}$.

Figure 3:
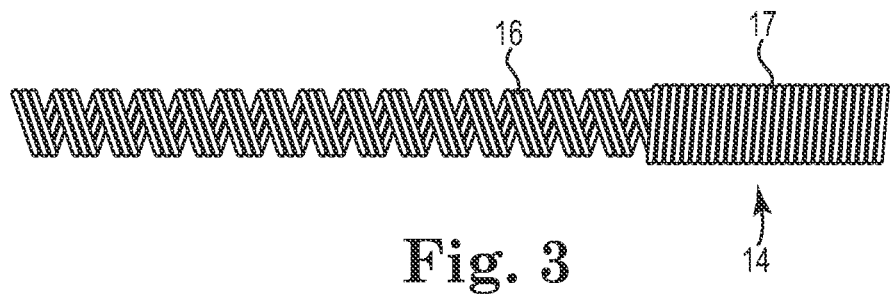
FIG. 3 illustrates a filler layer over the stranded coil of a medical lead in accordance with one embodiment.

FIG. 3 illustrates filler layer 17 is assembled over a portion of distal section 14 of medical lead 10 over inner coil 16. In one embodiment, filler layer 17 is a single inner strand, and in others it is a multifiler coil and in another is a ribbon or similar form. In one embodiment, filler layer 17 ends adjacent the end of inner coil 16, and in other embodiments the two ends can be offset from each other.

Figure 4A:
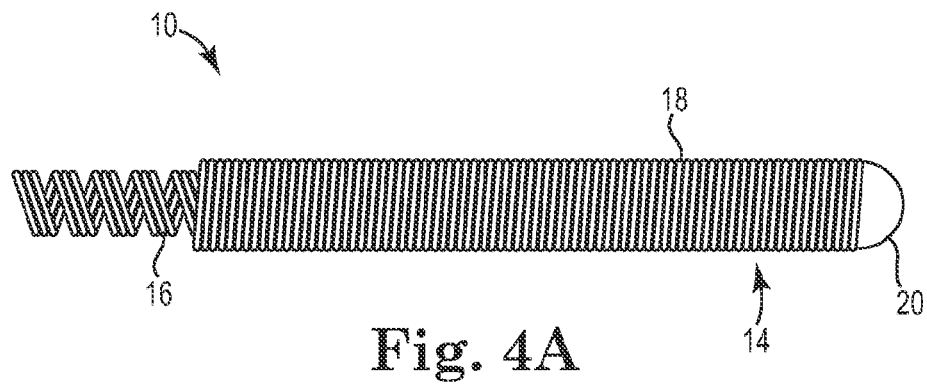
FIG. 4A illustrates a perspective view of a medical lead in accordance with one embodiment.

Marker coil 18 is then assembled over filler layer 17, as illustrated in FIG. 4A. In one embodiment, providing filler layer 17 between inner coil 16 and marker coil 18 provides a more stable and secure medical lead 10.

Figure 4B:
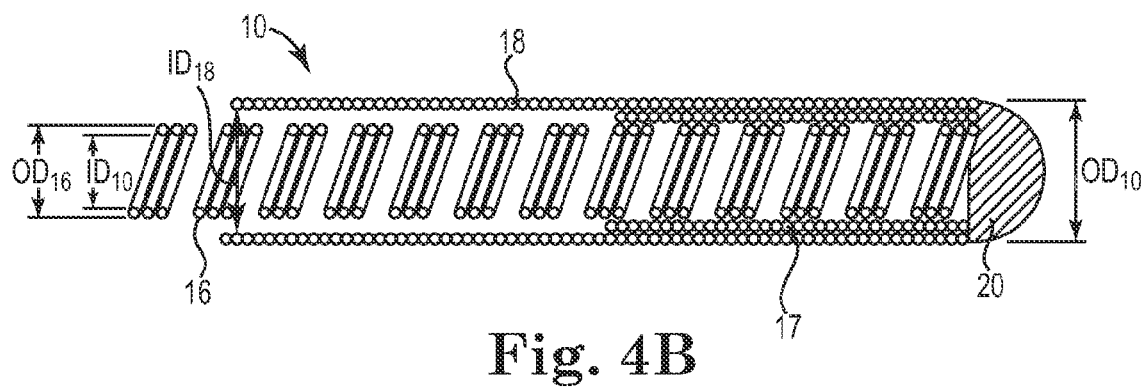
FIG. 4B illustrates a sectional view of a medical lead in accordance with one embodiment.
Figure 4C:
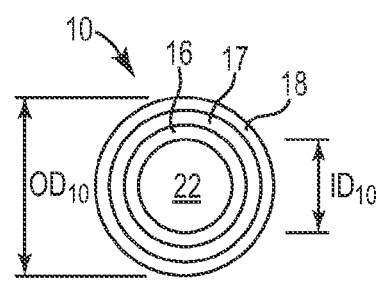
FIG. 4C illustrates a cross sectional view of a medical lead in accordance with one embodiment.

FIGS. 4B and 4C respectively illustrate cross sections taken parallel and perpendicular to the axis running along the length of medical lead 10. Inner coil 16 is illustrated defining lumen 22 (FIG. 4C). Filler layer 17 is assembled over inner coil 16 and marker coil 18 is assembled over inner coil 16. In one embodiment, lead tip 20 is a ball weld that is welded to each of the ends of inner coil 16, filler layer 17, and marker coil 18. In one embodiment, the overall outer diameter $OD_{10}$ of medical lead 10, along with the ends of the three coils— inner coil 16, filler layer 17, and marker coil 18—is such that a good weld is made between lead tip 20 and the coils 16 and 18.

Where only a inner coil 16 and a marker coil 18 are used, occasionally the lead tip 20 does not weld well to the ends of the coils 16 and 18. In some applications, dimensional requirements for the various components of medical lead 10 can degrade these welds. For example, where the outer diameter $OD_{10}$ of medical lead 10 and thickness of marker coil 18 establish a marker coil inner diameter $ID_{18}$ that is significantly larger than the inner coil outer diameter $OD_{16}$, this leaves a gap between inner coil 16 and a marker coil 18. With such as gap, there may be a degraded weld of the lead tip 20 to inner coil 16 and marker coil 18. Adding filler layer 17 can increase the surface area to which lead tip 20 is welded, and can improve the look and strength of the weld.

In one embodiment, inner coil 16 is stainless steel, such as SS316L, filler layer 17 is stainless steel, such as SS304 and marker coil 18 is one of gold, platinum, platinum alloy, platinum-iridium, palladium, tantalum, tungsten alloy, and a plastic material loaded with a radiopaque additive.

In one example, the pull strength was tested for a weld on a lead tip in a lead where only an inner coil and a marker coil were used. In that case, the pull strength for the weld was approximately 1.4667 lbs. The pull strength was also tested for the weld on lead tip 20 welded to each of the ends of inner coil 16, filler layer 17, and marker coil 18 in medical lead 10 in accordance with one embodiment. In that case, the pull strength for the weld was approximately 1.71033 lbs, or approximately a 15% improvement with filler layer 17.

In one embodiment, medical lead 10 is configured for applications of very small dimensions. In one example, inner diameter of inner coil 16, and thus the inner diameter $ID_{10}$ of the central lumen 22 of medical lead 10, is approximately 0.009 inch, the thickness of inner coil 16 is approximately 0.006 inch, the thickness of filler layer 17 is approximately 0.0025 inch, and the thickness of marker coil 18 is approximately 0.004 inch. As such, the outer diameter $OD_{10}$ of medical lead 10 is approximately 0.034.

In one application, providing a medical lead 10 having the inner diameter $ID_{10}$ of the central lumen 22 of approximately 0.009 inch and having an outer diameter $OD_{10}$ of approximately 0.034 is workable for the application. As such, if filler layer 17 is not used in such an application, either or both of inner coil 16 or marker coil 18 must have larger thicknesses or the outer diameter $OD_{10}$ cannot be maintained. Filler layer 17 allows maintaining the outer diameter $OD_{10}$ to be maintained while still allowing the above given thicknesses of the coils to be maintained.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of forming a medical lead comprising:
    forming a first wire coil with a first outer diameter and having an end;
    removing a coating from a distal section at the end of the first wire coil thereby creating a second outer diameter in the distal section, the second outer diameter being less than the first outer diameter;
    forming a second wire coil over at least the second outer diameter of the distal section of the first wire coil thereby filling an area around the second outer diameter of the first wire coil in the distal section and at the end of the first wire coil;
    forming a marker coil over the first and second wire coils at least over the distal section and at the end of the first wire coil and the end of the second wire coil; and
    forming a single ball weld at a distal end of the medical lead where the ends of each of the first and second wire coils and the marker coil are coupled creating an electrical coupling.

2. The method of claim 1 wherein removing the coating from the distal section of the first wire coil allows the first wire coil to function as a conductor and electrode in the medical lead.

3. The method of claim 1, wherein forming the marker coil comprises including a radiopaque material capable of producing a relatively bright image on a fluoroscopy screen.

4. The method of claim 1, wherein the distal section of the first wire coil is at a distal end of the medical lead such that the ball weld is formed at the distal end.

5. The method of claim 1, wherein forming a first wire coil comprises forming a multifiler stranded coil.

6. A medical lead comprising:
    a first wire coil having an outer diameter and an end;
    a marker coil having an inner diameter and an end, the marker coil assembled over the first wire coil such that their ends are aligned;
    wherein the outer diameter of the first wire coil is smaller than the inner diameter of the marker coil thereby defining a gap at the ends of the first wire and the marker coil;
    a second wire coil with an end and substantially filling the gap between the first wire coil and the marker coil; and
    a single ball weld formed at a distal end of the medical lead, thereby coupling together the ends of the first wire coil, the second wire coil and the marker coil.

7. The medical lead of claim 6, wherein the ball weld is formed at a distal end of the medical lead.

8. The medical lead of claim 6, wherein the inner diameter of the marker coil is less than 0.03 inch.

9. The medical lead of claim 6, wherein the medical lead is one of a group comprising an endoscopic device, laproscopic device, embolic protection device, and guidewire.

10. The medical lead of claim 6, wherein the marker coil comprises a radiopaque material capable of producing a relatively bright image on a fluoroscopy screen.

11. The medical lead of claim 10, wherein the marker coil comprises one of a group of material comprising gold, platinum, platinum-iridium, palladium, tantalum, tungsten alloy, and a plastic material loaded with a radiopaque additive.

12. The medical lead of claim 6, wherein the first and second coils comprise stainless steel.

13. A medical lead comprising:
   a first wire coil having a first outer diameter at a first portion and having a second outer diameter at a second portion located at its end;
   a marker coil having an inner diameter, the marker coil assembled over the first and second portions of the first wire coil;
   wherein the second outer diameter of the first wire coil is smaller than the inner diameter of the marker coil thereby defining a gap adjacent the second portion of the first wire coil at the end of the first wire coil and an end of the marker coil;
   a second wire coil substantially filling the gap between the first wire coil and the marker coil adjacent the second portion of the first wire coil; and
   a single ball weld formed at a distal end of the medical lead thereby coupling together the ends of the first wire coil, the second wire coil, and the marker coil.

14. The medical lead of claim 13, wherein the ball weld is formed at a distal end of the medical lead.

15. The medical lead of claim 13, wherein the inner diameter of the marker coil is less than 0.03 inch.

\* \* \* \* \*